US007601546B2

(12) United States Patent
Bayloff et al.

(10) Patent No.: US 7,601,546 B2
(45) Date of Patent: Oct. 13, 2009

(54) DIAGNOSTIC TEST DEVICES

(75) Inventors: Simon W. Bayloff, Skipton (GB); Michelle Del Bono, Barnoldswick (GB); Maurice C. Biott, Keighley (GB); Sylvia Lindsay-Watt, Steeton (GB)

(73) Assignee: Systagenix Wound Management (US), Inc., Wilmington, DE (US)

( * ) Notice: Subject to any disclaimer, the term of this patent is extended or adjusted under 35 U.S.C. 154(b) by 0 days.

(21) Appl. No.: 10/590,248

(22) PCT Filed: Feb. 23, 2005

(86) PCT No.: PCT/GB2005/000680

§ 371 (c)(1),
(2), (4) Date: Apr. 26, 2007

(87) PCT Pub. No.: WO2005/082254

PCT Pub. Date: Sep. 9, 2005

(65) Prior Publication Data

US 2007/0244368 A1     Oct. 18, 2007

Related U.S. Application Data

(60) Provisional application No. 60/587,861, filed on Jul. 15, 2004.

(30) Foreign Application Priority Data

| Feb. 23, 2004 | (GB) | ................................. 0403976.4 |
| Feb. 23, 2004 | (GB) | ................................. 0403978.0 |
| Jan. 28, 2005 | (GB) | ................................. 0501818.9 |

(51) Int. Cl.
*G01N 33/53*        (2006.01)

(52) U.S. Cl. ............................ 436/514; 422/58; 422/59; 422/61; 422/102; 436/518; 436/165; 436/174; 435/287.1

(58) Field of Classification Search ............. 422/58–61, 422/102; 436/518, 514, 165, 174; 435/287.1
See application file for complete search history.

(56) References Cited

U.S. PATENT DOCUMENTS 4,976,923 A * 12/1990 Lipsky et al. ................. 422/58

(Continued)

FOREIGN PATENT DOCUMENTS

WO    WO 2005/044110 A    5/2005

OTHER PUBLICATIONS

Veronese, F.M. et al. "Bioconjugation in pharmaceutical chemistry", IL Farmaco 54, 497-516 (1999).

(Continued)

*Primary Examiner*—Bao-Thuy L Nguyen
(74) *Attorney, Agent, or Firm*—Morgan, Lewis & Bockius, LLP

(57)    ABSTRACT

A diagnostic test apparatus comprising: a shaft having a first end and a second end; a swab or a biopsy punch mounted on the first end of a shaft; and a cap for fitting over the first end of the shaft, said cap containing at least one diagnostic test reagent; wherein the shaft comprises at least one cap engagement element located proximate to the first end, said element extending radially outwardly of the swab or the biopsy punch for engagement with the cap to retain the cap on the shaft. Also provided are diagnostic caps for use in the test apparatus having a small internal volume and at least one diagnostic test reagent located in or on an absorbent plug inside the cap. Also provided are diagnostic caps for use in the test apparatus having a housing extending from a sample receiving port, said housing defining a lateral flow path for the sample. Also provided is a test system comprising a swab shaft, a biopsy punch shaft and a diagnostic cap in accordance with the invention, wherein the cap can be used interchangeably between the two different shafts.

14 Claims, 2 Drawing Sheets

U.S. PATENT DOCUMENTS

| | | | |
|---|---|---|---|
| 4,999,163 A * | 3/1991 | Lennon et al. | 422/58 |
| 5,026,653 A * | 6/1991 | Lee et al. | 436/518 |
| 5,084,245 A * | 1/1992 | Berke et al. | 422/61 |
| 5,119,830 A * | 6/1992 | Davis | 600/584 |
| 5,139,742 A * | 8/1992 | Heijink | 422/58 |
| 5,266,266 A | 11/1993 | Nason | |
| 5,429,804 A * | 7/1995 | Sayles | 422/58 |
| 5,770,229 A | 6/1998 | Tanihara et al. | |
| 5,800,779 A * | 9/1998 | Johnson | 422/58 |
| 6,083,460 A * | 7/2000 | Morikawa et al. | 422/56 |
| 6,248,294 B1 | 6/2001 | Nason | |
| 6,524,530 B1 | 2/2003 | Igarashi et al. | |
| 2002/0085953 A1* | 7/2002 | Parker | 422/61 |

OTHER PUBLICATIONS

Ulbrich, K. et al. "Polymeric drugs based on conjugates of synthetic and natural macromolecules" Journal of controlled release 64, 63-79 (2000).

* cited by examiner

US 7,601,546 B2

DIAGNOSTIC TEST DEVICES

CROSS-REFERENCE TO RELATED APPLICATIONS

This application is a National Stage application under 35 U.S.C. 371 of PCT/GB2005/000680, filed Feb. 23, 2005, which claims priority from GB0403976.4 filed Feb. 23, 2004, GB0403978.0 filed Feb. 23, 2004, U.S. 60/587,861 filed Jul. 15, 2004 and GB0501818.9 filed 28 Jan. 2005.

FIELD OF THE INVENTION

The present invention relates to diagnostic test caps for use with swab and biopsy punch systems.

BACKGROUND OF THE INVENTION

Absorbent swabs are generally known in the medical arts for use in collecting fluid specimens from a patient for further analysis. Medical swabs commonly comprise a fibrous swab tip at one end of an elongated stick or shaft which is manually handled to contact the swab tip with a selected part of a patient, for example the surface of a wound. As a result, some tissue fluid, including cellular matter, adheres to the swab tip which can then be contacted with one or more selected reagents to indicate the presence of infection or other information regarding patient condition. Tests commonly performed with swab specimens include fluorescent tests, enzymatic tests, monocolonal antibody based tests and agglutination tests.

Still greater diagnostic accuracy can sometimes be achieved by analysis of a biopsy sample. Typically, the biopsy sample may be taken by means of a cylindrical, sharpened biopsy punch located at one end of an elongated stick or shaft which is manually punched into the tissue of interest. The punch sample is then homogenized and analysed with suitable reagents to arrive at a diagnosis.

In accordance with standard techniques, the collected biological specimen (swab or biopsy) is normally transferred from the swab tip or the biopsy punch to a slide or other laboratory apparatus such as a test tube or the like for contact with selected reagents and further analysis. However, it can be difficult to ensure transfer of a sufficient specimen quantity from the swab tip to the laboratory slide or test tube to ensure accurate test results. Contamination of the sample can accidentally take place during the transfer, and delays between the time of specimen collection and actual test performance can also result in a decrease in test reliability. The need for a separate analysis step also increases the overall cost of the diagnostic procedure.

U.S. Pat. No. 5,266,266 describes a diagnostic swab having a hollow swab shaft extending between a swab tip adapted to collect a targeted specimen and a break-off nib that protrudes into a reservoir of reagent solution. Following collection of a sample on the swab tip, deformation of the reservoir is effected to sever the nib from the swab to open the rear end of the swab shaft and permit reagent flow from the reagent chamber through the swab shaft to the swab tip. The swab is fully enclosed in a housing having a cap, in which may be provided a further reagent, such as treated beads, for reaction with the eluate from the swab tip. This swab arrangement requires quite large amounts of thermoplastic molding material for its construction, and quite large amounts of reagent solution for satisfactory operation, with resulting increased cost and loss of sensitivity due to dilution of the swab sample.

U.S. Pat. No. 6,248,294 describes a self-contained diagnostic swab arrangement comprising a conventional swab and a diagnostic housing to receive and enclose the swab after collection of a sample. The diagnostic housing includes a reservoir of reagent liquid, and a diagnostic test strip extending up one side of the housing. This diagnostic swab arrangement requires quite large amounts of thermoplastic molding material for its construction, and an excessive amount of reagent solution for satisfactory operation.

SUMMARY OF THE INVENTION

The present invention relates to extremely compact diagnostic measurement and display configurations that can be fitted inside such a small cap, thereby minimizing the overall size of the apparatus, reagent usage, and sample dilution, as will be made clear in the following discussion.

DETAILED DESCRIPTION OF THE INVENTION

Figure 1:
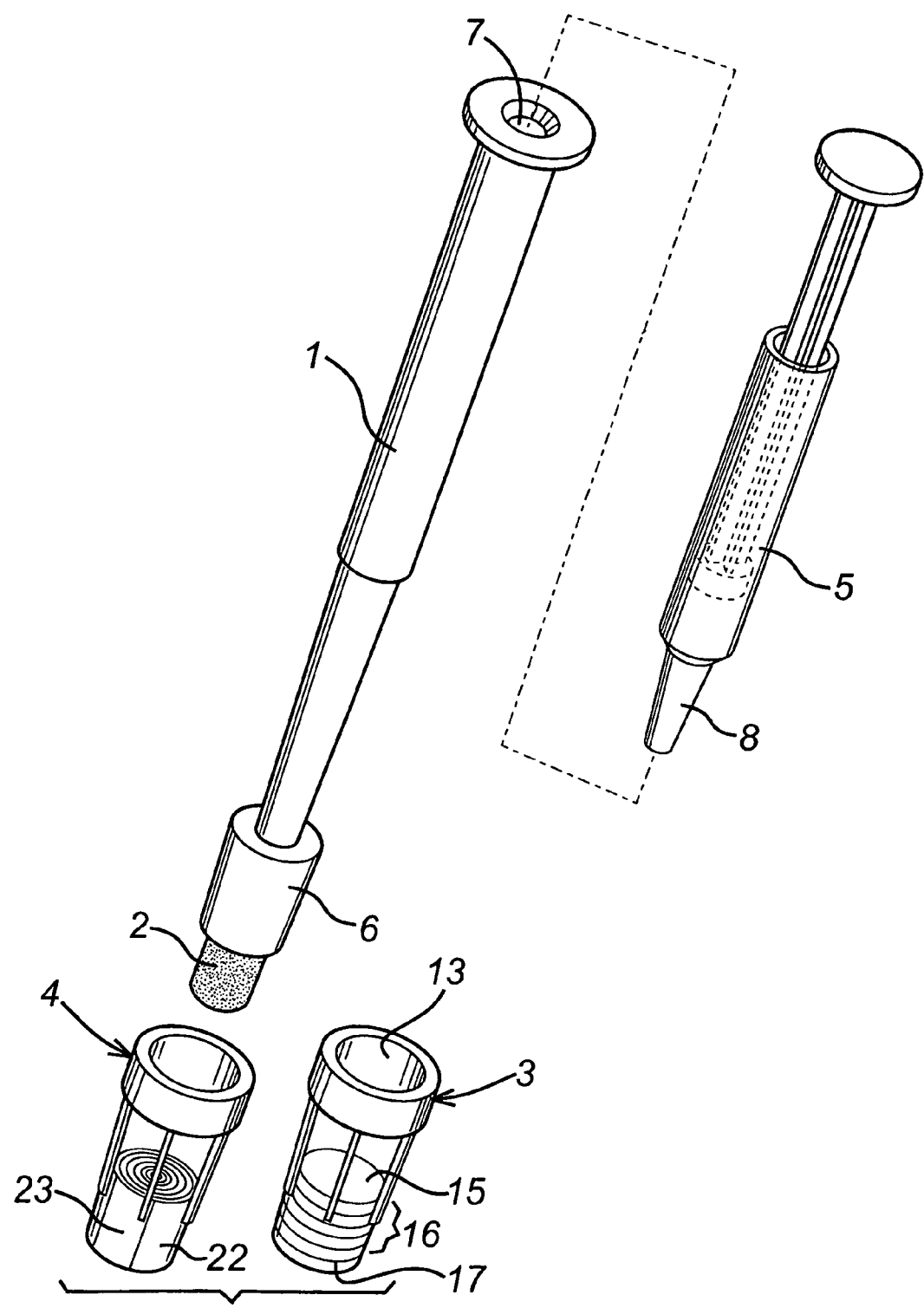
FIG. 1 shows an apparatus comprising a swab, two diagnostic caps according to the present invention, and a syringe for introducing fluid into the swab shaft.

The diagnostic test caps according to the invention are suitable for use in a diagnostic test apparatus comprising: a shaft having a first end and a second end; a swab or a biopsy punch mounted on the first end of a shaft; and a diagnostic cap according to the present invention for fitting over the first end of the shaft; wherein the shaft comprises at least one cap engagement element located proximate to the first end, said element extending radially outwardly of the swab or the biopsy punch for engagement with the cap to retain the cap on the shaft.

The use of a shaft that is adapted in this way to enable fitting of a cap near to the first end allows the use of a small diagnostic cap according to the present invention with the apparatus. This provides for economy of materials usage.

The cap engagement element on the shaft for fitting of the cap is typically located from 1 mm to about 30 mm from the base of the swab or the biopsy punch. This is consistent with the use of the relatively small diagnostic caps described.

The cap engagement element on the shaft for fitting of the cap may a tapered region of the shaft for forming an interference fit with the cap, for example it may appear as a truncated cone that is coaxial with the shaft and tapers towards the first end of the shaft. Or the whole shaft may have a diameter larger than that of the swab or biopsy punch, with a tapered region adjacent to the first end. In any case, the diameter of the tapered region where it engages with the cap is greater than the diameter of the swab or biopsy punch, so that the cap can be fitted over the swab or biopsy punch.

In other embodiments, the cap engagement element may comprise a snap-fitting projection for forming a snap-fit with one or more complementary projections on an inner surface of the cap, or a threaded projection for forming a screw fit with one or more complementary threads on an inner surface of the cap. Accordingly, the caps according to the present invention may comprise a suitably tapered inner surface for forming an interference fit with the shaft as described above, or the caps may comprise a snap-fitting projection for forming a snap-fit with one or more complementary projections on an outer surface of the shaft, or a threaded projection for forming a screw fit with one or more complementary threads on an outer surface of the shaft.

The swab may be any absorbent swab, for example a nonwoven fibrous swab. Typically the diameter of the swab is about 2 to about 5 mm, for example about 3 mm. In certain embodiments, the swab may be formed from a medically acceptable open-celled foam, for example a polyurethane foam, since such foams have high absorbency and can readily be squeezed to expel absorbed fluids. The biopsy punch will typically be a stainless steel cylindrical punch of diameter about 1 mm to about 10 mm, for example about 3 mm to about 8 mm, typically about 6 mm.

In certain embodiments the shaft is hollow, whereby a fluid can be passed down the shaft from the second end to expel a biological sample from the swab or the biopsy punch into the cap for diagnostic analysis. The shaft may comprise a fitting at the second end for attachment of a syringe or other source of the fluid. In certain embodiments, the apparatus may comprise a reservoir of liquid attached to the second end of the shaft, for example a compressible bulb containing the liquid, which can be activated after use of the swab or biopsy punch. Suitable devices of this kind are described, for example in U.S. Pat. No. 5,266,266, the entire content of which is incorporated herein by reference.

Another advantage of the hollow shaft is that, where the apparatus is a biopsy punch, the biopsy sample can more readily be pushed or blown out of the punch. The biopsy punch apparatus can further comprise a homogenizing tool that can be passed down the hollow shaft to homogenize a tissue sample in the biopsy punch. This step of homogenizing can be followed, if necessary, by passing liquid down the shaft from the second end to expel the homogenized tissue from the biopsy punch into the cap for diagnostic analysis.

Suitably, the cap has a length of from about 1 cm to about 4 cm, for example from about 15 mm to about 25 mm. Suitably, the cap has an internal diameter of from about 1 mm to about 10 mm, for example from about 2 mm to about 6 mm. It follows that the internal volume of the cap when it is secured on the shaft is small, suitably from about 10 $mm^3$ to about 1000 $mm^3$, for example from about 50 $mm^3$ to about 300 $mm^3$. This small volume permits diagnostic tests to be carried out on small samples, for example with little or no dilution of samples collected by a typical swab or biopsy punch.

Suitably, a venting aperture is provided in a lower region of the cap, for example in the base of the cap. This assists smooth flow of the biological sample from the swab or biopsy punch into the cap for diagnostic testing.

Suitably, the cap is at least partially transparent. This allows visible diagnostic indicators to be observed through the cap without removing the cap. In some embodiments the cap is at least partially transparent to ultraviolet light, for example light having wavelength 300-350 nanometers.

The caps according to the present invention contain compact diagnostic test devices that can be used to analyse one or more diagnostic indicators in samples having a small volume. Suitably, the caps contain at least one diagnostic test reagent provided in or around an absorbent plug located within the body of the cap. Suitably, the absorbent plug has an uncompressed volume of from about 10 to about 1000 $mm^3$, for example from about 50 to about 300 $mm^3$. The absorbent plug effectively wicks the analyte solution to the diagnostic indicators in the cap.

The diagnostic caps according to the present invention preferably contain a plurality of diagnostic test reagents for detecting a plurality of different analytes. Preferably, the plurality of different test reagents are located in radially or axially spaced-apart relation inside the cap, so that color changes (or other changes) caused by the presence or absence of different analytes can readily be distinguished.

For example, in some embodiments the at least one diagnostic test reagent is provided in or on an annular diagnostic strip extending at least part of the way around the inside of the cap, and preferably the whole way around the inside of the cap. The strip (or strips) may be segmented into a plurality of regions adapted to detect different diagnostic indicators, whereby these regions are radially spaced around the inside of the cap. The strip (or strips) may be wrapped around an absorbent plug located within the body of the cap, whereby the absorbent plug wicks the fluid under test to the strip or strips. It has been found that an especially suitable plug for this kind of wicking is provided by a cylindrical bundle of hydrophilic fibers, such as hydrophilic polyester fibers.

In other embodiments, at least one diagnostic test reagent is provided in or on a diagnostic sheet extending transversely across the inside of the cap. The edges of the sheet appear then as a ring through the side walls of the cap. A stack of such sheets may make up a plug inside the cap, and different sheets in the stack may be adapted to indicate the presence of different biological markers. Preferably, the sheets are made of absorbent material such as filter paper, so as to draw fluid sample from the swab or the biopsy punch.

The diagnostic material in the cap preferably undergoes a color change (the term color change includes chemiluminescence and/or a change in appearance under UV light) in the presence of one or more analytes, and preferably this color change is visible through the side wall of the cap. The diagnostic cap itself may bear radially and/or axially spaced indicia corresponding to the different regions or layers of diagnostic material inside the cap.

Suitably, the cap may be provided with a filter that is located between the swab or biopsy punch and the diagnostic material when the cap is secured on the shaft in use. The filter may be any paper or microporous film suitable for separating solid debris from the analyte solution to be passed to the diagnostic material.

Suitably, the cap may be provided with a fill indicator. That is to say, a means to indicate when the diagnostic material or materials have all been wetted by the analyte solution. For example, the fill indicator could be a sheet of filter paper in the base of the cap that has been treated to change color when wetted by the analyte solution.

Analytes that could be detected by the diagnostic caps according to the present invention include, but are not limited to, the group selected from pH, redox potential, free radical activity, activated oxygen, $Fe^{3+}$; endogenous proteases such as matrix metalloproteinase, elastase, collagenase and gelatinase; other enzymes such as lysozyme, acid hydrolases, lactate dehydrogenase, glycosidases, cathepsins B, L, D, G, plasmin, plasminogen activator and trypsin-like enzymes; kallikreins; indicators of wound infections such as lipopolysaccharides, in particular phospholipase A protein, or outer membrane proteins, such as omp T; protease inhibitors such as TIMPs, PAIs, alpha 1 antitrypsin, macroglobulin; cytokines such as TNFalpha; Interleukins such as IL-1, Il-6, IL-10; growth factors including GM-CSF, VEGF, PDGF, TGF-beta, IGF; soluble growth factor receptors; cytokine antagonists; soluble VEGF receptor IL-1 receptor antagonist; matrix components or fragments thereof, such as glycosaminoglycans including hyaluronic acid, collagen peptides, fibronectin fragments, fibrin (ogen) fragments; cell surface receptors (especially for tissue biopsy) such as CD44, Integrins, PDGF-receptor, plasminogen/u-PA receptors; and chemotractant molecules including leukotriene B4, C5A, and formylated peptides.

In suitable embodiments, the diagnostic material in the apparatus of the present invention comprises a pH-indicator or a redox indicator. Low pH and high oxidative stress are both characteristics of infected or chronic wounds. Colorimetric pH indicators bound to solid substrates, such a universal indicator papers, are well known in the art. Redox indicators include substances that undergo a color change in the presence of reactive oxygen species such as superoxide or hydroxyl radicals. One such indicator molecule is diphenylpicrylhydrazyl, which undergoes a color change from purple to colorless in the presence of free radicals.

In suitable embodiments, the diagnostic material in the apparatus to the present invention contains one or more immunological binding partners to bind the one or more analyte molecules present in the sample. The immunological binding partners may for example comprise monoclonal or polyclonal antibodies, antibody fragments, or chimeric antibodies. Alternatively, the immunological binding partners may comprise antigens in cases where the presence of predetermined antibodies in the sample is being mapped. Preferably, the immunological binding partners comprise monoclonal antibodies. Preferably, the immunological or other binding partners are immobilised on a solid support material, for example by avidin-biotin linking, or dialdehyde derivatization of the support material, followed by cross-linking to a peptide binding partner. Other immunological binding partners and/or reagents or indicator molecules may be present in the solution optionally used to expel the sample from the swab or biopsy punch as hereinbefore described.

The solid support materials immunological or other binding partners may be used in a range of immunoassays to map the presence of biologically active molecules. For example, the support having antibodies or antibody fragments bound thereto may be used in sandwich immunoassay-type mapping. Alternatively, the support may have analog ligands bound to the antibodies, whereby the molecules present in the wound fluid are detected by affinity displacement immunoassay. Various other immunoassays will be apparent to persons skilled in the art.

The analytes of interest may include enzymes that can modify substrates, for example proteins or polypeptides, by cleavage. Such modification of peptide substrates can be detected to determine the presence or absence of the analyte in a sample. Accordingly, in suitable embodiments, the diagnostic material in the apparatus of the present invention comprises a chemiluminescent, chromogenic or fluorogenic substrate for an enzyme analyte present in the sample.

One method for detecting the modification of a substrate by an enzyme is to label the substrate with two different dyes, where one dye serves to quench the fluorescence of the other dye by fluorescence resonance energy transfer (FRET) when the dye molecules are in close proximity. A typical acceptor and donor pair for resonance energy transfer consists of 4-[[-(dimethylamino)phenyl]azo]benzoic acid (DABCYL) and 5-[(2-aminoethylamino] naphthalene sulfonic acid (EDANS). EDANS is excited by illumination with 336 nanometer light, and emits a photon with a wavelength of 490 nanometers. If a DABCYL moiety is located within 2 nanometers of the EDANS, this photon will be efficiently absorbed. DABCYL and EDANS can be attached to opposite ends of a peptide in the diagnostic material used in the systems of the present invention. If the peptide is intact, FRET will be very efficient. If the peptide has been cleaved by an enzyme analyte, the two dyes will no longer be in close proximity and FRET will be inefficient. The cleavage reaction can be followed by observing either a decrease in DABCYL fluorescence or an increase in EDANS fluorescence (loss of quenching).

Another suitable diagnostic material comprises a chromogenic dye conjugated to a solid support by a suitable cleavable substrate moiety, such as a peptide. The chromogenic dye will change color when the linker group is cleaved by the analyte of interest. For example, para-nitrophenyl is colorless when linked to the support, and turns yellow when cleaved. The analyte concentration can be determined by measuring absorbance at 415 nanometers. Other dyes that produce detectable color change upon cleavage are known to those skilled in the art.

In yet another embodiment, the diagnostic material may comprise a colored support having a differently-colored molecule conjugated thereto by a linker moiety that can be cleaved by an analyte, for example an enzyme in the sample. Cleavage of the dye from the colored support can thereby result in a color change of the diagnostic material.

The solid support materials used for the above identified assays of enzyme activity and immuno-assays may comprise any suitable natural or synthetic polymer, including insoluble polysaccharides such as cellulose, and synthetic polymers such as polyacrylates. The cleavable cross-linkages where present generally comprise cleavable oligopeptidic sequences or cleavable oligosaccharides, each typically of twenty residues or fewer, for example from 3 to 15 residues.

The sensitivity of the diagnostic material will depend on a number of factors, including the length of the cleavable linker sequences. Steric hindrance may also be reduced by coupling the cleavable oligopeptidic sequence to the polymer by means of an appropriate spacer. Thus, the oligopeptidic sequences may couple the polymers directly (in which case the cross-linkage consists of the oligopeptidic sequence) or by means of an appropriate spacer. Suitable conjugation methods incorporating spacers are described in U.S. Pat. No. 5,770,229.

The following paper gives a useful review of bioconjugation techniques for use in pharmaceutical chemistry: Veronese, F. M. and Morpurgo, M (1999) Bioconjugation in Pharmaceutical chemistry II Farmaco, 54, 497-516 and Ulbrich, K., et al (2000) Journal of controlled release 64, 63-79. The entire contents of these papers are hereby incorporated by reference.

The present invention is especially suitable for detection of a wide variety of enzymes in biological samples. Typically, the enzyme is selected such that elevated levels of the enzyme in a wound fluid are associated with pain, wound infection or wound chronicity. Usually, the enzyme is a protease, and the linker group comprises an oligopeptidic sequence which is a substrate for the protease.

In certain embodiments, the proteases to be detected may include elastase. Elastase levels are elevated in a range of wound healing disorders, including infected wounds and chronic wounds. In such embodiments, suitable substrate linkers may include one or more of the oligopeptidic sequences lys-gly-ala-ala-ala-lys -Ala-Ala-Ala-, Ala-Ala-Pro-Val, Ala-Ala-Pro-Leu, Ala-Ala-Pro-Phe, Ala-Ala-Pro-Ala or Ala-Tyr-Leu-Val.

In certain embodiments, the proteases to be detected may include a matrix metalloproteinase, in particular MMP-2 or MMP-9. These matrix metalloproteinases are elevated in chronic wounds such as venous ulcers, diabetic ulcers and pressure sores. In these embodiments, the cleavable linker may comprise the oligopeptidic sequence -Gly-Pro-Y-Gly-Pro-Z-, -Gly-Pro-Leu-Gly-Pro-Z-, -Gly-Pro-Ile-Gly-Pro-Z-, or -Ala-Pro-Gly-Leu-Z-, where Y and Z are amino acids.

In certain embodiments, the proteases to be detected may include a collagenase. Collagenase is elevated in chronic wounds such as venous ulcers, diabetic ulcers and pressure sores. In these embodiments, the cleavable linker may comprise the oligopeptidic sequence -Pro-Leu-Gly-Pro-D-Arg-Z-, -ProLeu-Gly-Leu-Leu-Gly-Z-, -Pro-Gln-Gly-Ile-Ala-Gly-Trp-, -Pro-Leu-Gly-Cys (Me)-His-, -Pro- Leu-Gly-Leu-Trp-Ala-, -Pro-Leu-Ala-Leu-Trp-Ala-Arg-, or -Pro-Leu-Ala-Tyr-Trp-Ala-Arg-, where Z is an amino acid.

In certain embodiments, the proteases to be detected may include a gelatinase. Gelatinase is elevated in chronic wounds such as venous ulcers, diabetic ulcers and pressure sores. In these embodiments, the cleavable linker may comprise the oligopeptidic sequence -Pro-LeuGly-Met-Trp-Ser-Arg-.

In certain embodiments, the proteases to be detected may include thrombin. In these embodiments, the cleavable linker may comprise the oligopeptidic sequence -Gly-Arg-Gly-Asp-, -Gly-Gly-Arg-, -Gly-Arg-Gly-Asp-Asn-Pro-, -Gly-Arg-Gly-Asp-Ser-, -Gly-Arg-Gly-Asp-Ser-Pro-Lys-, -Gly-Pro-Arg-, -Val-Pro-Arg-, or -Phe-Val-Arg-.

In certain embodiments, the proteases to be detected may include stromelysin. In these embodiments, the cleavable linker may comprise the oligopeptidic sequence -Pro-TyrAla-Tyr-Trp-Met-Arg-.

In certain embodiments, the proteases to be detected may include a kallikrein. The term "a kallikrein" refers to all serine proteases, whose activation is associated with the degradation of kininogen to form kinins, which are implicated in the onset of pain. Suitable peptide sequences for use in cleavable substrates for kallikrein include -Phe-Arg-Ser-Ser-Arg-Gln- or -Met-Ile-Ser-Leu-Met-Lys-Arg-Pro-Gln- that can be degraded by kallikrein at Lys-Arg or Arg-Ser bonds.

In addition to the proteases, it is also envisaged that the enzyme could be, for example, an antibacterial chitinase or chitosanase such as lysozyme (elevated in infected wounds), in which case the substrate for the enzyme would be a polysaccharide or oligosaccharide comprising D-glucosamine or N-acetyl D-glucosamine residues.

Particularly preferred diagnostic indicators for use in the systems of the present invention are described in pending U.S. patent applications 60/444,523 filed 31, Jan. 2003, 60/444,521 filed 31, Jan. 2003, 60/516,692 filed 3, Nov. 2003 and 60/516,688 filed 3 Nov. 2003, the entire contents of which are incorporated herein by reference.

It will be appreciated that the use of the diagnostic caps according to the present invention may involve additional reaction steps in order to detect the desired analytes. For example, the caps may be treated with further reagents, for example the caps may be treated with one or more reagents in situ on the shaft hereinbefore described by passing the reagents through the hollow shaft.

It is an advantage of the diagnostic caps according to this invention that they can be used interchangeably on a range of different swabs and biopsy punches provided that they have suitable elements for securing the cap onto the shaft thereof. This kind of system allows the medical practitioner to choose between a range of alternative swab or biopsy sampling methods according to clinical choice, while carrying out the same diagnostic tests on the sample obtained by either method, and furthermore using only a single type of diagnostic cap.

The diagnostic caps may also be sterilized, but this is not generally necessary because the caps do not come into contact with the patient being diagnosed. It is an important advantage of the invention that the diagnostic caps do not need to be sterilized in the same way as the swab/biopsy punch with which they are used. This feature greatly expands the range of diagnostic chemistry available, since a number of assay chemistries, such as antibody-based assays, can be degraded by the conditions used to sterilize medical articles.

Specific embodiments of the present invention will now be described further, by way of example, with reference to the accompanying drawings.

Figure 2:
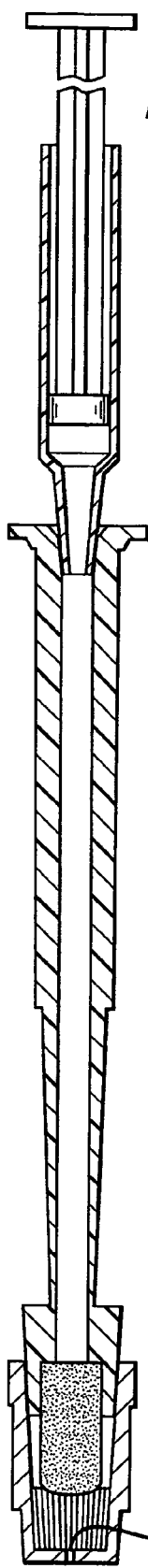
FIG. 2 shows the embodiment of FIG. 1 in longitudinal cross-section, with a diagnostic cap and the syringe secured on the swab shaft.

Referring to FIGS. 1 and 2, the swab comprises a hollow shaft 1, which is generally molded in one piece from thermoplastic polymer. A conventional swab pad 2 of medically acceptable sponge or nonwoven fibers is secured to a first end of the shaft 1, in fluid communication with the hollow interior of the shaft 1.

The apparatus further comprises two alternative diagnostic caps according to the present invention 3, 4. The caps 3, 4 each can form a snug interference fit with an expanded region 6 of the swab shaft. The expanded region 6 has a frusto-conical cross-section that is complementary to the internal cross-section of the openings of the caps 3, 4. In particular, it can be seen that the projection region 6 extends radially outwardly of the swab 2. As a result, the caps 3, 4 according to the present invention are quite small.

At the top of the hollow shaft 1 is there is an opening 7 that can form a liquid-tight interference fit with the nozzle 8 of syringe 5. The syringe 5 may be filled with gas, and used simply to blow a liquid sample out of the swab 2 into the diagnostic cap 3, 4. Alternatively, the syringe 5 may contain water, saline or buffered saline to wash the sample out of the swab 2 into the cap 3, 4. In yet another embodiment, the syringe 5 may contain a diagnostic reagent in aqueous solution. In yet other embodiments, the apparatus may comprise a plurality of syringes 5 containing different aqueous solutions, for example different aqueous reagents for carrying out the desired analysis in the cap. It will be appreciated that the syringes 5 do not need to be sterile, since they are not applied to the patient.

Figure 3:
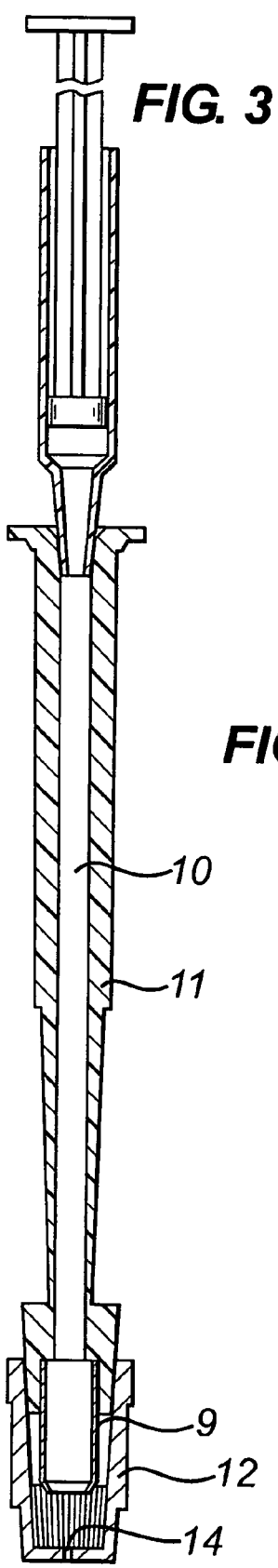
FIG. 3 shows a longitudinal cross-section through a biopsy punch attached to a diagnostic cap according to the present invention.
Figure 4:
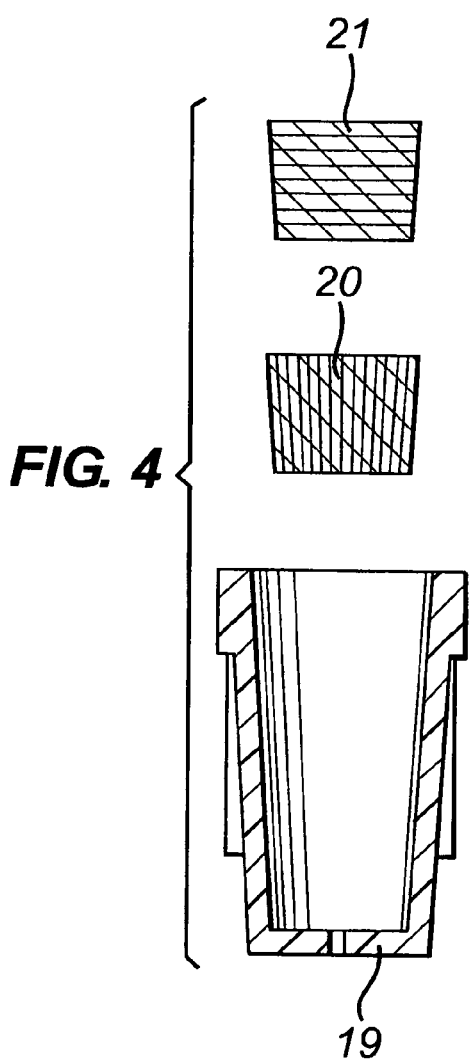
FIG. 4 shows a longitudinal cross-section through an embodiment of a second diagnostic cap according to the present the invention.

Referring to FIG. 3, the structure of the biopsy punch is substantially identical to that of the swab shown in FIGS. 1 and 2, except that swab pad 2 has been replaced by a stainless-steel biopsy punch 9. In use, a homogeniser (not shown) may be passed down the bore 10 of shaft 11 to homogenise the biopsy punch sample before or after attachment of the diagnostic cap 12.

The structure of diagnostic cap 3 will now be described in more detail. The diagnostic cap 3 is formed by injection molding from a transparent polymer, such as polyethylene terephthalate (PET), polymethylmethacrylate (PMMA), or a transparent polyvinyl chloride (PVC). In certain preferred embodiments the cap is transparent both to UV radiation and 300-350 nanometers, and to visible radiation. This can be achieved, for example, with some transparent PVC plastics. The cap 3 has an opening 13 at the top that is shaped to form a liquid-tight interference fit on projection 6 of the swab shaft 1. A small gas-venting aperture 14 is provided in the bottom of cap 3 to assist the flow of the sample from the swab 2 into the cap 3. The lower part of the cap 3 is occupied by a stack of liquid-permeable disks 15, 16, 17. These disks include a filtration layer 15 for removing solid and cellular debris from the sample, diagnostic layers 16 each of which undergoes a color change in the presence of a different predetermined analyte, and a fill indicator layer 17, which undergoes a color change when wetted. The total amount of liquid required to wet all of the diagnostic layers 16 and the indicator layer 17 is only about 100 microliters, whereby little or no dilution of the sample collected on the swab is needed in order to carry out the diagnostic analysis for multiple analytes. Furthermore, it can be seen from FIGS. 2 and 3 that, in use, the diagnostic swab contacts the absorbent diagnostic layers in the cap 3, whereby a liquid sample in the swab can wick directly into those layers.

Diagnostic cap 4 comprises a transparent cap body similar to that of cap 3. However, instead of a stack of sensor disks 16 as shown in cap 3, cap 4 has a segmented annular diagnostic strip 20 inserted into the lower part thereof. The annular strip 20 comprises a plurality of radially spaced stripes 22, 23 having sensitivity to different analytes in the sample. Color changes in these stripes 22, 23 are readable through the transparent sides of the cap. A plug 21 is inserted inside the annular diagnostic strip 20 to wick the fluid sample from the swab to the diagnostic strip 20. The plug 21 is made up of a bundle of hydrophilic polyester filaments aligned substantially coaxially with the cap. This bundle also serves to filter solids and cellular debris from the sample before it reaches the diagnostic strip 20. The advantages of this arrangement are similar to those of cap 3, but even less of the relatively expensive diagnostic reagents are needed to form the strip 20. It is also possible that an even more compact cap suitable for even smaller fluid samples can be made by providing the plug 21 with a cavity in the center thereof into which the swab 2 can be inserted.

The above embodiments have been described by way of example only. Many other examples falling within the scope of the accompanying claims will be apparent to the skilled reader.

What is claimed is:

1. A diagnostic cap comprising a substantially cup-shaped body, and absorbent plug located within the body, and at least one diagnostic test reagent, wherein the at least one diagnostic test reagent is provided in or on an annular diagnostic strip extending radially around the inside of the cap.

2. The diagnostic cap according to claim 1, wherein the cap has a length of from about 1 cm to about 4 cm.

3. The diagnostic cap according to claim 1, wherein the cap has one or more engagement elements on an inside surface of a side wall of the cap for securing the cap onto a shaft.

4. The diagnostic cap according to claim 3, wherein said engagement elements are selected from the group consisting of: a tapered region for forming an interference fit with a complementary tapered region on the shaft, a snap-fitting projection for forming a snap-fit with one or more complementary projections on the shaft, and a threaded projection for forming a screw fit with one or more complementary threads on the shaft.

5. The diagnostic cap according to claim 3, wherein a venting aperture is provided in a lower region of the cap.

6. The diagnostic cap according to claim 5, wherein the cap is at least partially transparent.

7. The diagnostic cap according to claim 3, wherein the absorbent plug has an uncompressed volume of from about 10 to about 1000 $mm^3$, preferably from about 50 to about 300 $mm^3$.

8. The diagnostic cap according to claim 3, wherein the cap bears radially and/or axially spaced indicia corresponding to different regions or layers of diagnostic material inside the cap.

9. The diagnostic cap according to claim 3, wherein the cap is provided with a filter for separating solid debris from an analyte solution to be passed to the diagnostic test reagent.

10. The diagnostic cap according to claim 9, wherein the cap is provided with a fill indicator to indicate when the diagnostic test reagent has been wetted by an analyte solution.

11. The diagnostic cap according to claim 10, wherein the diagnostic test reagent comprises a solid support material having a substrate moiety covalently linked thereto that is cleavable by an analyte enzyme.

12. The diagnostic cap according to claim 10, wherein the diagnostic test reagent comprises a solid support material having an immunological binding partner for an analyte moiety covalently linked thereto.

13. The diagnostic cap according to claim 10, wherein the cap contains a plurality of diagnostic test reagents for detecting a plurality of different analytes.

14. A diagnostic cap comprising a substantially cup-shaped body, an absorbent plug located within the body, and at least one diagnostic test reagent, wherein the at least one diagnostic test reagent is provided in or on a diagnostic sheet extending transversely across the inside of the cap.

* * * * *

UNITED STATES PATENT AND TRADEMARK OFFICE
CERTIFICATE OF CORRECTION

| | | |
|---|---|---|
| PATENT NO. | : 7,601,546 B2 | Page 1 of 1 |
| APPLICATION NO. | : 10/590248 | |
| DATED | : October 13, 2009 | |
| INVENTOR(S) | : Simon W. Bayliff et al. | |

It is certified that error appears in the above-identified patent and that said Letters Patent is hereby corrected as shown below:

On title page Items (12) and (75) Simon W. "BAYLOFF" should be changed to Simon W. --BAYLIFF--.

Signed and Sealed this

Twenty-ninth Day of December, 2009

David J. Kappos
*Director of the United States Patent and Trademark Office*